United States Patent
Tournier et al.

(10) Patent No.: US 6,706,280 B2
(45) Date of Patent: *Mar. 16, 2004

(54) CARBOXYLATED PHOSPHATIDIC ACID ESTERS

(75) Inventors: Hervé Tournier, Valleiry (FR); Bernard Lamy, St. Julien en Genevois (FR)

(73) Assignee: Bracco Research S.A., Geneva (CH)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 149 days.

(21) Appl. No.: 09/373,983

(22) Filed: Aug. 16, 1999

(65) Prior Publication Data

US 2002/0136760 A1 Sep. 26, 2002

(30) Foreign Application Priority Data

Aug. 19, 1998 (EP) .............................. 98810801

(51) Int. Cl.⁷ ...................... A61K 9/127; C07F 9/02
(52) U.S. Cl. .................... 424/450; 424/417; 428/402.2; 554/79
(58) Field of Search ................ 424/450, 1.21, 424/9.321, 9.51, 417; 554/79; 428/402.2; 935/54

(56) References Cited

U.S. PATENT DOCUMENTS

| | | | | |
|---|---|---|---|---|
| 4,348,386 A | * | 9/1982 | Kojima | 424/101 |
| 4,830,858 A | * | 5/1989 | Payne | 424/450 |

* cited by examiner

*Primary Examiner*—Gollamudi S. Kishore
(74) *Attorney, Agent, or Firm*—Nixon & Vanderhye P.C.

(57) ABSTRACT

Novel compounds of formula

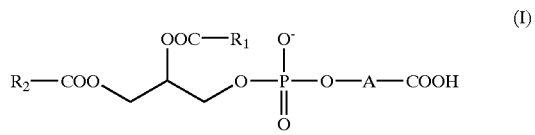

(I)

in which $R_1$ and $R_2$ are phospholipid fatty acid residues and A is an aliphatic and/or cycloaliphatic hydrocarbon chain optionally substituted by hydroxy and/or further carboxylic functions. The novel compounds are useful for making liposomes of enhanced stability and entrapping capacity.

11 Claims, No Drawings

CARBOXYLATED PHOSPHATIDIC ACID ESTERS

TECHNICAL FIELD

The present invention relates to phosphatidic acid esters of aliphatic and cycloaliphatic hydroxylated hydrocarbons substituted with carboxylic functions. These compounds are particularly useful in the fields of drug targeting with liposomes and MRI contrast media for diagnostics.

BACKGROUND ART

Aliphatic esters of diacyl-glycerophosphatidic acid (diacyl glycerophosphate esters) are well known since some of them, like phosphatidylethanolamine, phosphatidylcholine, phosphatidylinositol and phosphatidylglycerol, are natural phospholipid constituents of lecithins.

Synthetic esters of diacyl-glycerophosphatidic acid have been reported, for instance phosphatidyl esters of acyl and benzyl-substituted glycerol (CA 92-110494/13 and CA 94-046877/07) or an anti-retroviral diacylphosphatidic acid ester of the following hydroxy compound

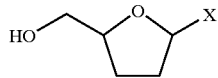

in which X is a nucleic base (van Wijk et al. *Biochim. Biophys. Acta* 1165 (1992), 45–52).

SUMMARY OF THE INVENTION

The present inventors have found that phosphatidic acid esters of formula

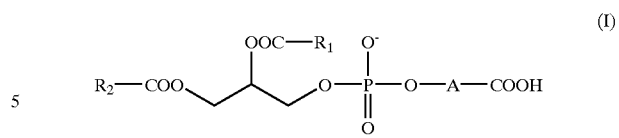

have the unexpected useful property of stabilizing phospholipids when in admixture therewith. For instance, when phospholipids are used to make liposomes, the presence of the phosphatidic acid esters improve the entrapping capacity of the liposomic vesicles, prevents vesicle coalescence, and inhibits leakage of the entrapped substances into the liquid carrier. In the above formula, $R_1$ and $R_2$ are phospholipid fatty acid residues and A is an aliphatic and/or cycloaliphatic hydrocarbon chain optionally substituted by hydroxy and/or further carboxylic functions. In a preferred embodiment —A—=—$(CH_2)_n$— where n is an integer of from 3 to about 14, preferably 5 to 10.

DETAILED DESCRIPTION OF THE INVENTION

The fatty acid residues $R_1$ and $R_2$ are preferably derived from saturated or unsaturated fatty acids commonly found in lecithins, for instance the acids lauric, myristic, palmitic, stearic, arachidic, oleic, linoleic, and the like.

According to a first method of preparation of compounds of formula

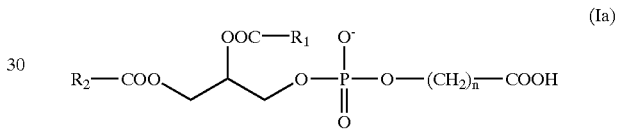

one can esterify a phosphatidic acid (II) with an acid-alcohol HO—A—COOH, for instance HO—$(CH_2)_n$—COOH (III), the acidic function of which is temporarily protected, for instance benzylated, and subsequent removal of the protective group; this is summarized in the following exemplifying scheme:

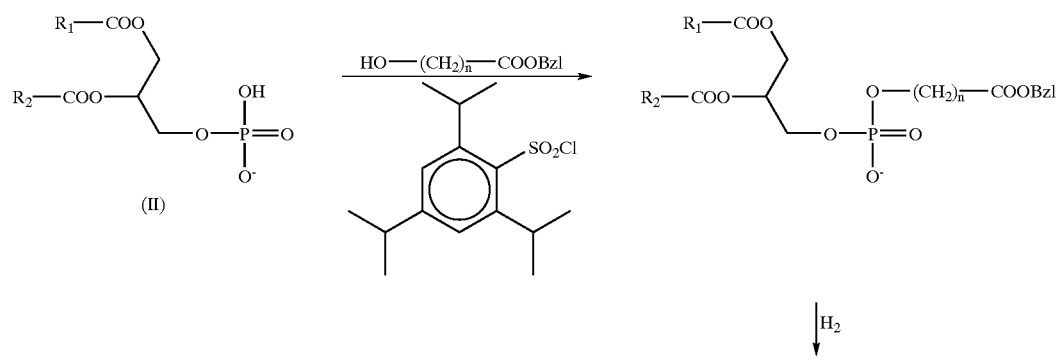

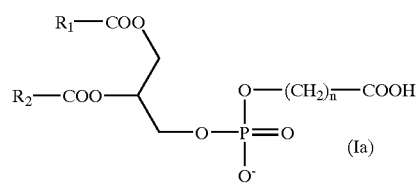

Benzylation of the acid alcohol (III) can be effected by reacting benzyl bromide with an alcali metal salt of (III) in DMF or hexamethyl phosphoramide (HMPT) as follows:

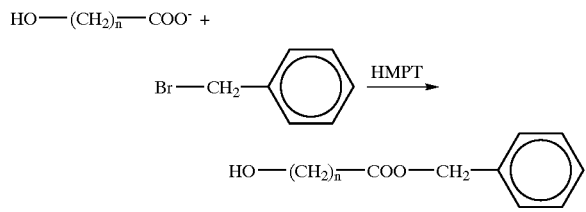

Of course this method is general and applies to other compounds of formula I using other acid-alcohols HO—A—COOH, the above embodiment scheme being for illustration only.

According to another route to prepare (Ia), one can react a bromo-acid Br—(CH$_2$)$_n$—COOH (IV) with the silver salt of the phosphatidic acid (II)

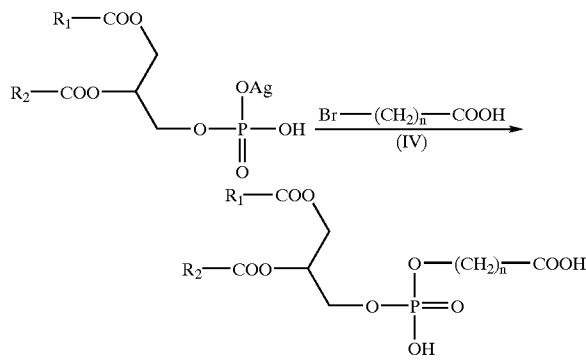

According to still another route, on can protect one of the free —OH of the phosphatidic acid (II), and thereafter react the product with the bromide (V) to give the compound (VI); the latter provides the acid-ester (IA) after deprotection by usual means. This is schematized as follows:

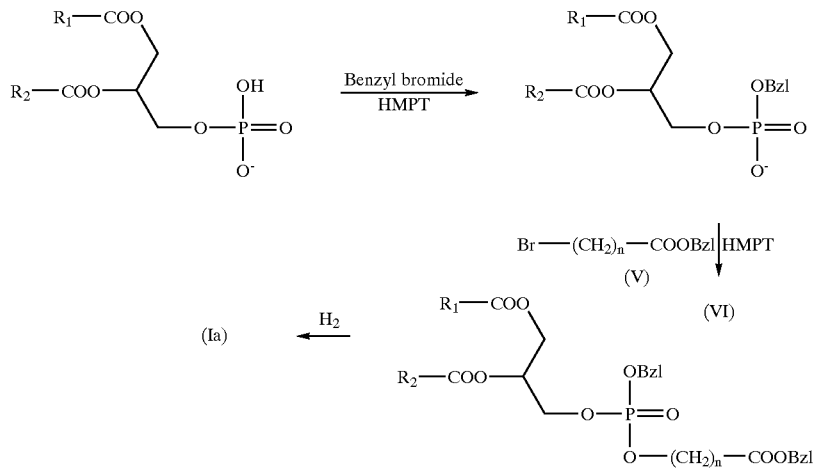

The direct reaction of the phosphatidic acid (II) with the bromide (V) is also possible as follows:

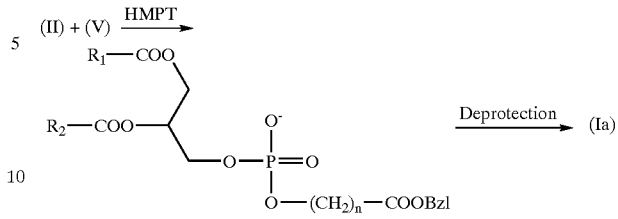

Of course, the above embodiments are not limiting, the disclosed methods being general and applicable using other intermediates of formulae Br—A—COOH and Br—A—COOBzl.

The new compounds disclosed are very useful to stabilize liposome vesicles in suspension in water, buffers and biological liquids against rupture and coalescence with time. They also increase their encapsulating capacity (enhanced weight ratio of encapsulated substance versus phospholipids making the vesicles) and stabilise the vesicle membrane against leakage of the entrapped substances toward the carrier liquid. For instance, in the case where liposome vesicles are used to carry iodinated x-ray opacifying media in the organism via the blood stream, incorporating a proportion of one or more of the novel compounds to the phospholipids making the liposomes will strongly decrease the tendency of the encapsulated iodine to be released into the blood by permeating the vesicle membrane; the efficiency of transport of the opacifying compounds to possibly remote organs in the body is thus markedly increased. Usually the effective proportion of the novel compounds in the liposome forming lipids is in the range of 1 to 25% by weight, but these values can be overcome if desired. The liposome forming lipids or mixture of lipids substantially include all compounds commonly used in the field of liposomes, i.e. glycerophospholipids, non-phosphorylated glycerides, glycolipids, sterols and other additives intended to impart modified properties to liposomic membranes. Preferably, they comprise at least a polarizable component, namely a cationic or anionic function carrying lipid or an ionizable surfactant such as a fatty alcohol diphosphate ester, e.g. dicetyl phosphate (DCP) or a higher alkyl amine like stearylamine (SA). Charged phospholipids, i.e. fatty acid glycerides phosphatides like phosphatidic acid (PA), phosphatidylglycerol (PG), phosphatidylinositol (PI), phosphatidylserine (PS) from natural sources or synthetic (such as dipalmitoylphosphatidic acid (DPPA), dipalmitoylphosphatidyl glycerol (DPPG), etc.) are convenient polarizable lipid components. The glycerophospholipids may include for instance dipalmitoyl-phosphatidylcholine (DPPC), dipalmitoylphosphatidylethanolamine (DPPE) and the corresponding distearoyl- and dimyristyl-phosphatidylcholine and -ethanolamine (DSPC; DSPE; DMPC and DMPE). The liposome forming phospholipids may also include natural phospholipids which have been subjected to more or less extensive hydrogenation, for instance egg and soy phosphatidylcholine.

The glycolipids may include cerebrosides, galactocerebrosides, glucocerebrosides, sphingomyelins, sulfatides and sphingolipids derivatized with mono-, di- and trihexosides. The sterols, which should be used with parsimony, as too much may impede membrane permeation, encompass cholesterol, ergosterol, coprostanol, cholesterol esters such as hemisuccinate (CHS), tocopherol esters and the like.

It has also been found that freeze dried phospholipid powders comprising phosphatidyl compounds of the invention may conveniently be stored for prolonged periods of time without loss of properties. This is particularly useful when these phospholipids are used for the manufacture of therapeutic or contrast agents or are incorporated in drug delivery vehicles that may further include targeting vectors.

Liposomes produced from the freeze dried powders containing the phosphatidyl compounds of the invention have shown the same improved stability and entrapping capacity observed for the liposomes prepared in the usual way from non freeze dried formulations.

The following Examples illustrate the invention in more details:

EXAMPLE 1

Ester of DPPA (dipalmitoylphosphatidic acid) with 6-hydroxycaproic acid

A). Benzyl-6-hydroxycaproate

In 200 ml of a water solution containing 0.22 mol of NaOH, one has slowly added under stirring between 4 and 8° C. 21.4 ml (0.2 mol) of g-caprolactone. After 4 hrs standing at room temperature (r.t.), the mixture was evaporated in the rotavapour and the resulting dry solid was washed by grinding with acetone. Yield: 29.47 g(96%) of sodium 6-hydroxycaproate to be stored in the dessicator under $P_2O_5$.

In 40 ml of HMPT were dissolved at 60° C. 7.7 g (50 mmol) of the foregoing sodium salt and 55 mmol of benzyl bromide were added under stirring. The mixture was further agitated for 2 hrs at 60° C., then it was left aside overnight. The mixture was diluted with 100 ml of water and the solution extracted by successively 100 and 200 ml of ether. After washing the combined extracts with 2×100 ml of water and drying over $Na_2SO_4$, they were evaporated to provide 1.26 g of the desired product in liquid form. This product contained relatively few impurities as ascertained by thin layer chromatography (TLC) on silicagel (hexane/ether 1:3). Further purification was effected by extracting the impurities with 3 successive portions of 60 ml of hexane at 60° C., then cooling to 4° C. and the upper hexane layers being discarded. The liquid residue was dried and further analyzed by TLC. The 1H-NMR spectrum was in complete accord with the structure of the desired compound.

B). Benzyl dipalmitoylphosphatidylhexanoate (DPPA$^-$Na.C$_6$.OBzl)

There were dispersed at 60° C. by sonication in 20 ml of chloroform 1.34 g (2 mmol) of DPPANa; then the dispersion was allowed to cool to room temperature. Another solution was prepared by dissolving 0.88 g (4 mmol) of the benzyl hydroxycaproate prepared in the previous step in 20 ml of dry pyridine, then adding 1.82 g (6 mmol) of triisopropylbenzene-sulfonyl chloride (TPS-Cl). The second solution was added drop-wise to the first solution and agitation was continued at room temperature for 1 hr, then it was heated for ½ hr at 50° C. After cooling it was treated with 2 ml of water and 20 ml acetone and heated for an additional ¾ hr at 50° C.

After evaporating the volatile solvents, the residue was diluted with 50 ml of water and the acidic solution brought to pH 6.5 by the careful addition of 1.26 g of NaHCO$_3$; then the pH was further raised to 9–9.5 with 1N NaOH and the water was progressively removed by azeotropic distillation with toluene (4 successive 50 ml portions). The residue was dispersed in 100 ml hexane and filtered. The collected solid, 2.47 g, was P-free according to TLC analysis and discarded. After evaporation, the filtrate afforded 2.61 g of solid which was dissolved in 40 ml of hexane, and the solution was poured over 52 g of silica (grade 60 for HPLC). The silica was dried under vacuum and washed by two successive portions of 120 ml of water (Buchner filtration). The wet silica was again dried on the rotavapor and taken in 120 ml of a CHCl$_3$/MeOH (8:2) mixture; then the silica was filtered out and the filtrate was evaporated to give 2.2 g of solid. This solid was crystallized from 150 ml of boiling ethanol (cooling to r.t., then in the refrigerator to 4° C.). The crystallized solid was drained, washed with cold EtOH and acetone and dried; yield 1.3 g (76%). The product was pure according to the TLC analysis (silica 60F$_{254}$; CHCl$_3$/MeOH/H$_2$O 65:25:4).

C). Dipalmitoylphosphatidyl-O-hexanoic acid

In a mixture of 15 ml EtOH and 135 ml AcOEt were dissolved by heating 3.13 g (3.6 mmol) of the benzyl dipalmitoylphosphatidyl-O-hexanoate described under B), then there were added 3 g of Pd/C hydrogenation catalyst and 10 ml of cyclohexene. The mixture was heated at 60° C. under agitation for an hour, after which it was cooled and the active C was removed by filtration. The filtrate was further cleaned by passing through a 0.2 μm micropore filter and evaporated to give 2.73 g of product which was recrystallized in 100 ml EtOH. Final yield of pure dipalmitoylphosphatidyl-O-hexanoic acid was 2.34 g (86%).

EXAMPLE 2

Ester of DPPA (dipalmitoylphosphatidic acid) with 8-hydroxyoctanoic acid

A). Benzyl-8-bromoctanoate

There were dissolved 11.6 g (52 mmol) of 8-bromooctanoic acid in 100 ml of CCl$_4$ and around 5° C. (ice bath), there were added to the solution 5.41 g (50 mmol) of benzyl alcohol and 2.5 mmol of 4-pyrrolidino-pyridine catalyst. Thereafter, a solution of 10.73 g (52 mmol) of dicyclohexylcarbodiimide (DCC) in 10 ml of carbon tetrachloride was added portion-wise under stirring. The precipitation of the expected dicyclohexylurea (DCU) was effective after a few min and the temperature was allowed to come back to room temperature. After ½ hr, the reaction was complete as checked by TLC (hexane/ether 1:1). Then after about 1 hr, 0.5 ml of AcOH were added to quench remaining DCC and the DCU was filtered out after about one hour (yield 11.2 g=100%).

The solution was washed by successive liquid portions of extractants as follows:

2×100 ml of water (to remove the acetic acid);
2×100 ml of 1N $NaHCO_3/Na_2CO_3$ solution (pH 9,5) to remove the un-reacted bromoacid;
100 ml 1N $NaHCO_3$ solution;
100 ml half-saturated NaCl solution;
50 ml of saturated NaCl solution.

The purified carbon tetrachloride solution was filtered on a phase separator paper, dried on anhydrous $MgSO_4$ and evaporated to dryness which left a clear liquid from which some residual DCC crystallized on standing. This product was pure enough for use in the following preparation sequences.

B). Benzyl ester of DPPA (Na salt)

There were dispersed in 50 ml DMF 6.71 g (10 mmol) of DPPA.Na and under violent stirring, 1.4 g (10 mmol) of triethylamine $NEt_3$) and 2.7 ml (22 mmol) of benzyl bromide were added. The mixture was agitated for 24 hrs at 70° C., then, after cooling, it was diluted with 300 ml ether and filtered (the solid was identified by TLC as mixture of NaBr and unreacted DPPA.Na). The ether filtrate was washed with 2×100 ml of HCl 0.1 N and the washing liquid reextracted with 100 ml ether. This extract was combined with the main ether phase and the whole was again washed with successive 50 ml portions of 1N $NaHCO_3$ and saturated NaCl. After filtration (0.92 g of un-reacted DPPA.Na), the ether solution was dried and evaporated, thus providing 6.77 g of product which was dispersed in 350 ml of acetone. After grinding the insoluble fraction and agitating at the boil, the dispersion was filtered hot and allowed to cool to room temperature, then to 4° C. overnight. The solid which crystallized out was re-crystallised once more in the same conditions, which finally afforded 4.72 g of the desired product.

C). Benzyl ester of DPPA (Ag salt)

The following preparations are to be carried out in the dark as much as possible. One mmol (761 mg) of DPPA.Na.OBzl, i.e. the product obtained under B) above was dissolved in 110 ml of acetone at the boil, then after cooling, an aqueous solution of silver nitrate (0.17 g $AgNO_3$ in a mixture of 5 ml $H_2O$ and 15 ml acetone) was added dropwise. After heating, the mixture was allowed to crystallize overnight in the dark; there were collected 0.79 g (93%) of solid.

D). Benzylated DPPA ester of benzyl 8-hydroxyoctanoate (DPPA.OBzl.$C_8$.OBzl)

In 2.5 ml of HMPT were dissolved 423 mg (0.5 mmol) of the DPPA.Ag.OBzl prepared in the previous step, then at 55° C., there were added under agitation 189 mg (0.6 mmol) of the benzyl-8-bromooctanoate obtained as described under A) above. The temperature was raised to 70° C. and a brown precipitate formed. After cooling, 20 ml of ether were added and the mixture was filtered; the filtrate was washed with successively 2×10 ml $H_2O$, 10 ml HCl 0.1 N, 10 ml $NH_4CO_3$ N (for the two last washing steps, separation of the layers had to be effected by centrifuging 10 min under 10,000 g), 10 ml saturated NaCl. Then the ether was dried as usual to give a solid which was used in the next step without further purification.

E). Dipalmitoylphosphatidyl-O-octanoic acid

The DPPA.OBzl.$C_8$.OBzl prepared as described in the previous step was deprotected by hydrogenation as disclosed in Example 1, step C. The product thus obtained had the same properties as that from Example 1, step C.

EXAMPLE 3
Dipalmitoylphosphatidyl-O-octanoic acid

A). Dipalmitoylphosphatidic acid Ag salt

In 1 ml of water there were dissolved 0.85 g (5 mmol) of $AgNO_3$; then the solution was diluted with 10 ml of MeOH and added in the dark under vigorous stirring to a solution of 3.35 g (5 mmol) of DPPA.Na in 350 ml of warm methanol. The mixture was cooled to 4° C., the precipitate formed was drained, washed with acetone and dried in the dark. Yield 3.67 g (97%).

B). Dipalmitoylphosphatidyl-O-octanoic acid-benzyl ester 1.675 g of DPPA.Na (2.5 mmol) were dissolved in 10 ml of HMPT and to this were added a solution of 1.56 g (5 mmol) of benzyl-8-bromooctanoate in 5 ml HMPT. The mixture was rotated and brought to 70° C. for 24 hrs, then overnight at room temperature. Then 60 ml of hexane were added and the solution was washed by 20 ml portions of successively: water 0.5M $NaHCO_3$, M $NaHCO3$, and saturated NaCl. After filtering on phase separation paper, the hexane was dried on magnesium sulfate, refiltered and evaporated, which gave 2.05 g of solid that was crystallized from acetone. Yield 1.09 g (46%).

C). Dipalmitoylphosphatidyl-O-octanoic acid

In a mixture of 4 ml EtOH and 30 ml AcOEt, there were dissolved at 60° C. 1.09 g (1.2 mmol) of benzyl-dipalmitoylphosphatidyl octanoate; 1 g of Pd/C and 2.5 ml of cyclohexene were added and the mixture was rotated for 1 hr at 60° C. After cooling the mixture was filtered, the collected catalyst was washed with chloroform/ethanol (8:2), and the combined filtrates evaporated to dryness. A solid was collected and crystallized from hot ethanol. Yield 0.45 g. The product was pure under TLC analysis.

If in the previous examples, the linear aliphatic reagents $HOC_{6-8}COOBzl$ and $BrC_{6-8}COOBzl$ were replaced by corresponding C4–5 and C9–14 compounds, the corresponding phosphatidyl acid esters were obtained accordingly.

Cycloaliphatic analogs were also obtained by similar techniques using for instance reagents such as

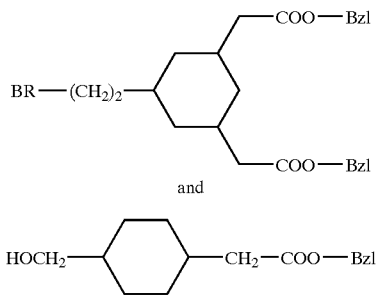

and

EXAMPLE 4

Three phospholipid mixtures numbered (A), (B) and (C) were prepared by admixing the ingredients described below.
(A):
SPC-3 (a hydrogenated soy lecithin from Lipoid, GmbH, Germany) 299 mg (61.7 mol %);
Cholesterol (from Fluka, Switzerland) 80.1 mg (33.3 mol %);
DPPA.Na (from Sygena, Switzerland) 20.9 mg (5.0 mol %);
total weight of lipids=400 mg.
(B):
SPC-3 299 mg (61.7 mol %);
Cholesterol 80.1 mg (33.3 mol %);
Dipalmitoylphosphatidyl-O-hexanoic acid 24.5 mg (5 mol %); total 403.6 mg.

(C):
SPC-3 275 mg (56.7 mol %);
Cholesterol 80.1 mg (33.3 mol %);
DPPA.Na 20.9 mg (5.0 mol %);
Dipalmitoylphosphatidyl-O-hexanoic acid 24.5 mg (5 mol %); total of lipids 400.5 mg.

Each of the above mixtures was diluted with 5 ml MeOH and 10 ml chloroform, after which the organic solution was thorougly dried by rotating overnight under reduced pressure at 35° C.

On the other hand an iodine solution was prepared from 52.24 g of iomeprol dissolved in 56.18 ml of water by heating, followed by ultrafiltration on 0.2 $\mu$m millipore membrane.

Iodine loaded MLV liposomes (A) to (C) were prepared by admixing 20 ml of the above iodine solution with 400 mg of each of the above dried lipid mixtures and stirring for ¾ hr at 65° C. The MLV (multilamellar vesicles) liposomes were then exhaustively extruded at 65° C. on polycarbonate membranes (4×2 $\mu$m, then 5×0.6 $\mu$m) for conversion to unilamellar vesicles (SUV) of enhanced entrapping capacity. Then the SUV liposome solutions were diluted with filtered (0.2 $\mu$m) Tris-buffer to make solutions containing 1 g/l Tris. One ml of each liposome preparation was further purified by dialysis against 2×1L phosphate buffer saline (PBS), then the average vesicle size, the lipid concentration, and the I/L (weight of iodine per weight of the lipids involved) were measured by usual means, e.g. as disclosed in EP-A-0 314 764. In the three cases the vesicle size was in the range of 370–400 nm, the lipid concentration about 20 mg/ml, and the I/L's were 2.7 (A), 3.2 (B) and 3.0 (C). The entrapment capacity of the liposomes made with the compounds of the invention was thus increased.

Stability in human plasma

One ml of the above liposome suspensions was diluted with 7 ml PBS and centrifuged for 25 min (46 000 g). After discarding the supernatant, the bottom residue was dialysed twice against 1 liter of PBS, then it was diluted with a little PBS to make 1 ml, i.e. to restore the initial lipid concentration (about 20 mg/ml). Then the dialyzed sample was admixed with 9 ml of human plasma and heated to 37° C. for incubation. The iodine released in the carrier liquid was determined by HPLC after diverse times of incubation (see the Table below). The results expressed in terms of percent of the original iodine released in time are provided in the next Table for samples of the (A), (B) and (C) liposome preparations in plasma (P1) and in PBS as control.

| Time | 0 (min) | | 15 (min) | | 30 (min) | | 60 (min) | | 120 (min) | |
|---|---|---|---|---|---|---|---|---|---|---|
| | PBS | P1 | PBS | P1 | PBS | P1 | PBS | P1 | PBS | P1 |
| (A) | 1.1 | 1.4 | 3.2 | 45.0 | 4.4 | 48.2 | 5.4 | 52.7 | 7.6 | 55.2 |
| (B) | 0.5 | 0.5 | 0.5 | 6.2 | 0.5 | 9.7 | 0.5 | 14.5 | 0.6 | 20.2 |
| (C) | 0.8 | 0.9 | 2.9 | 8.2 | 2.4 | 11.1 | 2.6 | 14.6 | 2.6 | 18.8 |

The foregoing results show that when the compounds of the invention are part of the phospholipids used to make liposomes, the stability of the vesicles is increased and the permeability to leakage of the liposomic membrane is reduced.

What is claimed is:

1. A phosphatidyl compound of the general formula

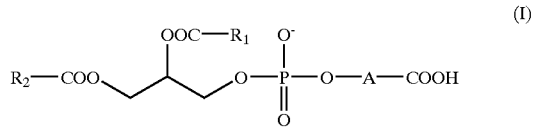

(I)

wherein $R_1$ and $R_2$ are phospholipid fatty acid residues and A is an aliphatic and/or cycloaliphatic hydrocarbon chain optionally substituted by hydroxy and/or further carboxylic functions in which —A—=—$(CH_2)_n$— where n is an integer of from 5 to 10.

2. The compounds of claim 1, in which n is 6–8.

3. A method for preparing a compound of claim 1, which comprises esterifying a phosphatidic acid (II) of formula $R_1COO$—$CH_2$—$CH(OOCR_2)$—$CH_2$—O—$PO_3H$ with an acid-alcohol HO—A—COOH, the acidic function of which is temporarily protected, and subsequent removal of the protective group as shown in the following scheme:

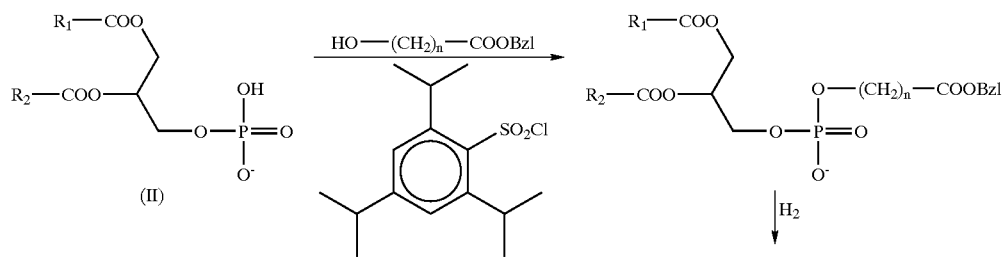

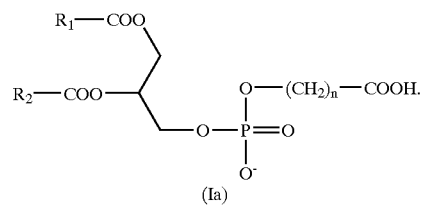

(Ia)

4. A method for preparing a compound of claim 1, which comprises reacting a bromo-acid Br—A—COOH, with a silver salt of the phosphatidic acid (II) of formula $R_1COO$—$CH_2$—$CH(OOCR_2)$—$CH_2$—O—$PO_3H$ according to the following reaction scheme

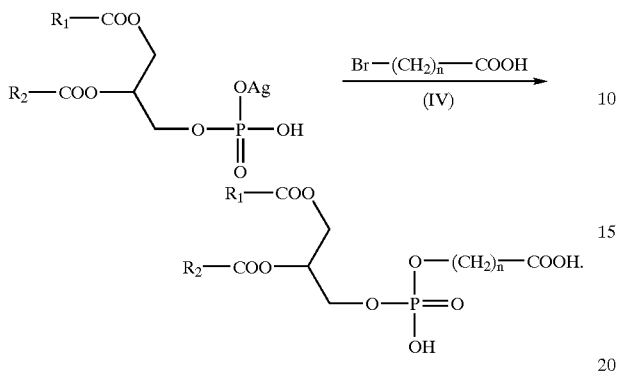

5. A method for preparing a compound of claim 1, which comprises protecting one of the free —OH of the phosphatidic acid (II), of formula $R_1COO$—$CH_2$—$CH(OOCR_2)$—$CH_2$—O—$PO_3H$ and thereafter react the product with a bromide Br—A—COOBzl, give the compound (VI); the latter providing the acid-ester (IA) after deprotection by the following scheme:

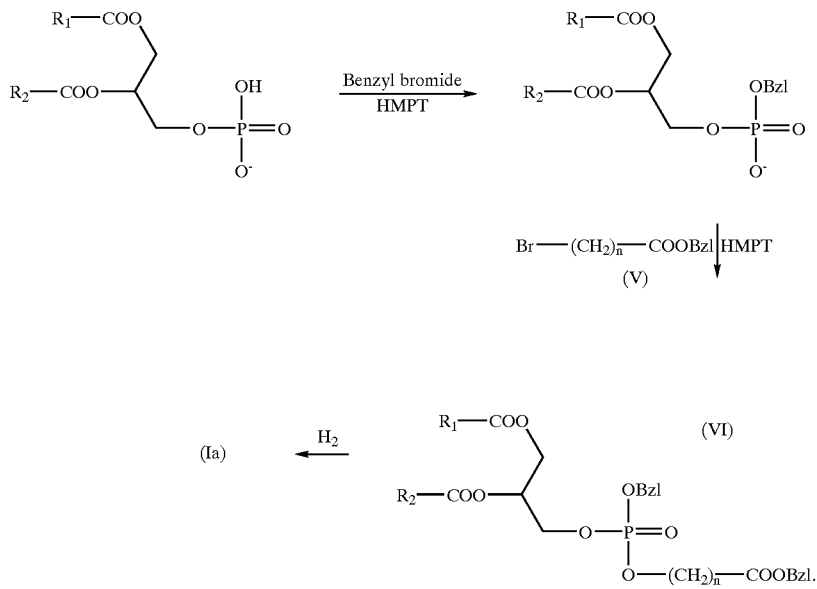

6. A freeze dried phospholipid powder comprising a phosphatidyl compound of claims 1.

7. Liposome vesicles of improved stability and entrapping capacity comprising phosphatidyl compounds of the general formula:

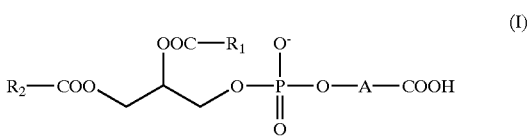

wherein $R_1$ and $R_2$ are phospholipid fatty acid residues and A is an aliphatic and/or cycloaliphatic hydrocarbon chain optionally substituted by hydroxy and/or further carboxylic functions in which —A—=—$(CH_2)_n$— where n is an integer of from 5 to 10.

8. Aqueous suspensions of liposomes of claim 7.

9. A therapeutic or contrast agent comprising an aqueous suspension of liposomes of claim 8.

10. The liposome vesicles of claim 7 in admixture with other phosphohpids.

11. The liposome vesicles of claim 7, in which n is 6–8.

* * * * *